United States Patent
Liang et al.

(10) Patent No.: US 12,291,737 B2
(45) Date of Patent: May 6, 2025

(54) SCHIZOCHYTRIUM STRAIN AND USE THEREOF, MICROBIAL OIL CONTAINING DHA AT SN-2 POSITION AND PREPARATION AND USE THEREOF

(71) Applicant: Hanpeng Qu, Hunan (CN)

(72) Inventors: Yun Liang, Hunan (CN); Sheng Cao, Hunan (CN); Shenjian Wang, Hunan (CN)

(73) Assignee: Hanpeng Qu, Changsha (CN)

( * ) Notice: Subject to any disclaimer, the term of this patent is extended or adjusted under 35 U.S.C. 154(b) by 0 days.

(21) Appl. No.: 17/375,551

(22) Filed: Jul. 14, 2021

(65) Prior Publication Data

US 2021/0340583 A1    Nov. 4, 2021

Related U.S. Application Data

(63) Continuation of application No. PCT/CN2020/130385, filed on Nov. 20, 2020.

(30) Foreign Application Priority Data

Nov. 26, 2019  (CN) .......................... 201911175787.4

(51) Int. Cl.
| | | |
|---|---|---|
| C12P 7/64 | (2022.01) | |
| C12N 1/12 | (2006.01) | |
| C12N 1/14 | (2006.01) | |
| C12P 7/6434 | (2022.01) | |
| C12P 7/6463 | (2022.01) | |
| C12P 7/6472 | (2022.01) | |

(52) U.S. Cl.
CPC .............. *C12P 7/6463* (2013.01); *C12N 1/14* (2013.01); *C12P 7/6434* (2022.01); *C12P 7/6472* (2013.01)

(58) Field of Classification Search
CPC ..... C12P 7/6463; C12P 7/6472; C12P 7/6427; C12N 1/14; C12N 1/12; C12N 1/125; C12R 2001/89; A23L 33/115; A23L 29/04; A23L 29/065
See application file for complete search history.

(56) References Cited

U.S. PATENT DOCUMENTS

2004/0052837 A1    3/2004  Stillwell

FOREIGN PATENT DOCUMENTS

| CN | 101346138 A | 1/2009 |
|---|---|---|
| CN | 103725721 A | 4/2014 |
| CN | 104011218 A | 8/2014 |
| CN | 109247397 A | 1/2019 |

OTHER PUBLICATIONS

Guo D-S. et al., "Development of a multi-stage continuous fermentation strategy for docosahexaenoic acid production by *Schizochytrium* sp.", Bioresource Technology, vol. 269, (2018), pp. 32-39. (Year: 2018).*
Chang G. et al., "Improvement of docosahexaenoic acid production on glycerol by *Schizochytrium* sp. S31 with constantly high oxygen transfer coefficient", Bioresource Technology, vol. 142, (2013), pp. 400-406. (Year: 2013).*
Raman K., Machine English translation of CN 104011218 A: "Microorganism Oil Rich In Polyunsaturated Fatty Acid", published on 80-27-2014 (Translation, total pp. 1-56). (Year: 2014).*
Li et al., "Enhanced arachidonic acid production from Mortierella alpina combining atmospheric and room temperature plasma (ARTP) and diethyl sulfate treatments", Bioresource Technology, vol. 177 (2015), pp. 134-140 (Year: 2015).*
He, Jianlin et al. "Synthesis of Sn-2 docosahexaenoic acid monoglyceride with immobilized lipase." Journal of the Chinese Cereals and Oils Association, Jan. 29, 2016: p. 76-80.
Lopes Paula A et al. "Docosahexaenoic acid (DHA) at the sn-2 position of triacylglycerols increases DHA incorporation in brown, but not in white adipose tissue, of hamsters." <<International Journal of Food Sciences and Nutrition>> vol. 69, No. 4, Dec. 31, 2018: p. 458-471.

* cited by examiner

Primary Examiner — Satyendra K Singh

(57) ABSTRACT

This disclosure relates to microbial technology, and more particularly to a *Schizochytrium* strain and a use thereof, a microbial oil containing DHA at an Sn-2 position, and a preparation and uses thereof. Sn-2 fatty acids of a triglyceride in the microbial oil contain 23% or more by weight of DHA. The microbial oil is prepared by fermentation using a *Schizochytrium* strain, where the *Schizochytrium* strain is *Schizochytrium* sp. with an accession number of GDMCC No. 60733.

3 Claims, No Drawings

SCHIZOCHYTRIUM STRAIN AND USE THEREOF, MICROBIAL OIL CONTAINING DHA AT SN-2 POSITION AND PREPARATION AND USE THEREOF

CROSS-REFERENCE TO RELATED APPLICATIONS

This application is a continuation of International Patent Application No. PCT/CN2020/130385, filed on Nov. 20, 2020, which claims the benefit of priority from Chinese Patent Application No. 201911175787.4, filed on Nov. 26, 2019. The content of the aforementioned application, including any intervening amendments thereto, is incorporated herein by reference in its entirety.

TECHNICAL FIELD

The present disclosure relates to microbial technology, and more particularly to a *Schizochytrium* strain and a use thereof, a microbial oil containing DHA at an Sn-2 position, and a preparation and a use thereof.

BACKGROUND

Docosahexaenoic acid (DHA) is a primary structural fatty acid in the brain and eyes, accounting for 97% and 93% of all n-3 fatty acids in the brain and eyes, respectively. It has been reported that the triglycerides with the Sn-2 position DHA are easier to be absorbed by intestinal mucosa. Meanwhile, it has also been demonstrated that when the intake of those lipids with the Sn-2 position DHA will make DHA most enriched in the brain, whereas when people take in lipids with DHA at other positions, of the highest level of DHA will occur in the liver, which indicates that triglycerides with different structures will experience different fatty acid metabolism routes, in other words, the fatty acids at the Sn-2 position can be more effectively absorbed than those at the Sn-1 or Sn-3 position. As a primary lipase, pancreatic lipase attaches to a water-oil interface to hydrolyze dietary fat molecules. Meanwhile, pancreatic lipase is specific to the hydrolysis of ester bonds at the Sn-1 and Sn-3 positions. As a consequence, after digested by pancreatic lipase, the triglyceride structure is converted into free fatty acids (from Sn-1 and Sn-3 positions) and a monoglyceride (formed by the glycerol skeleton and the Sn-2 fatty acid).The free fatty acids have difficulty in penetrating into bile salt micelle to be absorbed, and thus are prone to combining with calcium and magnesium ions in the intestine to form insoluble soap salts to be wasted, whereas the monoglyceride formed from the fatty acid at the Sn-2 position can easily penetrate into the bile salt micelle to be absorbed. Therefore, the absorption rate of fatty acids at the Sn-2 position in human body is higher than that of the fatty acids at the Sn-1 and Sn-3 positions.

As consumers become more aware of the health and function of DHA, microbial oils, as primary resources of DHA, have been largely adopted in infant food and nutraceuticals, and their nutritional benefits are increasingly recognized by public. Consequently, more and more attention has been paid to the absorption rate of DHA in microbial oils. More than 90% of the fatty acids in the microbial oil exist in the form of triglyceride, and the existing DHA-containing microbial oils are mainly produced by fermentation using *Ukenella, Schizochytrium, Thraustochytrium, Cryptodinium,* and yeast. However, the incorporation rate of DHA at Sn-2 position of the glycerol skeleton is far lower than that at the Sn-1 and Sn-3 positions, and a large amount of Sn-1 and Sn-3 DHA is converted into soap salts to be wasted, attenuating the benefits of the microbial oils.

SUMMARY

The object of the present disclosure is to provide a *Schizochytrium* strain and use thereof, a microbial oil containing DHA at an Sn-2 position and preparation and use thereof to solve the problem that human body has a poor adsorption to DHA in the microbial oil since DHA on the triglyceride in the microbial oil is dominated by Sn-1 and Sn-3 DHA. The *Schizochytrium* strain provided herein is *Schizochytrium* sp, and the microbial oil provided herein is produced through the fermentation using *Schizochytrium* sp, in which Sn-2 fatty acids of the triglyceride include 23% or more by weight of DHA, effectively improving the absorption of DHA in human body.

Technical solutions of this application are described as follows.

In a first aspect, the present disclosure provides a microbial oil, which comprises:
a triglyceride;
wherein Sn-2 fatty acids of the triglyceride contain 23% or more by weight of DHA.

In some embodiments, the microbial oil contains 38% or more by weight of DHA.

In a second aspect, the present disclosure further provides a method for producing the microbial oil mentioned above, comprising:
inoculating a *Schizochytrium* strain into a fermentation medium for fermentation to produce the microbial oil;
wherein the *Schizochytrium* strain has an accession number of GDMCC No. 60733.

In a third aspect, the present disclosure provides a microbial oil prepared by the above-mentioned method, comprising:
a triglyceride;
wherein Sn-2 fatty acids of the triglyceride contain 23% or more by weight of DHA.

In a fourth aspect, the present disclosure provides a food comprising the above-mentioned microbial oil, and the food is infant formula food, nutraceutical or health food.

In a fifth aspect, the present disclosure provides a *Schizochytrium* strain, where the *Schizochytrium* strain has an accession number of GDMCC No. 60733.

In a sixth aspect, the present disclosure provides a use of the *Schizochytrium* strain in the preparation of the above-mentioned microbial oil.

The *Schizochytrium* sp.-derived microbial oil provided herein is rich in DHA, and a weight percentage of DHA at the Sn-2 position of the triglyceride in total Sn-2 fatty acids is not less than 23%, which effectively facilitates the absorption and utilization of DHA in the microbial oil in human body.

The features and beneficial effects will be further described in detail below with reference to the embodiments.

Deposit of Microorganisms

The *Schizochytrium* strain used herein has been deposited in Guangdong Microbial Culture Collection Center (GDMCC, Guangdong Institute of Microbiology, $5^{th}$ Floor, No. 59 Building, No. 100 Xianliezhong Road, Guangzhou, China, 510070) on Aug. 8, 2019 with an accession number of GDMCC No. 60733.

DETAILED DESCRIPTION OF EMBODIMENTS

It should be noted that endpoints and values within ranges disclosed herein are only exemplary, and are intended to include any values close to these values or ranges. Any possible combination of values within the numerical range to form one or more new ranges should be considered to be expressly disclosed in this disclosure.

In a first aspect, the present disclosure provides a microbial oil, which includes a triglyceride, where Sn-2 fatty acids of the triglyceride include 23% or more by weight of DHA.

The DHA is abbreviation of docosahexenoic acid.

In some embodiments, a weight percentage of the triglyceride in the microbial oil is not less than 90%.

In some embodiments, a weight percentage of total DHA in the microbial oil is not less than 38%.

It should be understood that the total DHA is a total amount of DHA in the microbial oil, and can be measured according the method of GB 26400-2011. The contents of other fatty acids are measured according to the method of GB 5009.168-2016. Triglyceride DHA means that DHA is linked to the glycerol backbone through ester bonds.

In some embodiments, a weight percentage of DHA at the Sn-2 position of the triglyceride in the microbial oil is not less than 23%.

In some embodiments, a weight percentage of DHA at the Sn-2 position of the triglyceride in the microbial oil is not less than 23%, and a weight percentage of total DHA in the microbial oil is not less than 38%.

In a second aspect, the present disclosure further provides a method for producing the microbial oil mentioned above. A *Schizochytrium* strain is inoculated into a fermentation medium for fermentation, where an accession number of the *Schizochytrium* strain is GDMCC No.60733.

The strain for preparing the microbial oil can be obtained by a conventional method in the art.

The *Schizochytrium* strain provided herein is obtained by mutagenesis.

The mutagenesis is performed according to a conventional method, such as physical mutagenesis (ultraviolet mutagenesis, atmospheric room temperature plasma (ARTP) mutagenesis) and chemical mutagenesis.

In some embodiments, the mutagenesis is performed by ARTP mutagenesis.

The ARTP mutagenesis is carried out in a conventional mutagenesis system such as multifunctional mutagenesis system (MPMS) produced by Adhoc Interteck Co., Ltd. (Beijing, China).

The mutagenesis is performed according to conventional operations in the art. In an embodiment, the mutagenesis is performed at a plasma mutagenesis power of 80-120 W, a gas flow rate of 8-12 SLM (standard liter per minute) and a treatment distance of 1-3 mm.

The mutagenesis time is 5-60 s, preferably 15-30 s.

The mutagenesis is performed on a bacterial suspension with $OD_{600}$ of 0.6-0.8 or a bacterial concentration of $10^6$-$10^8$ cfu/mL.

In some embodiments, the mutagenesis is performed such that a lethality of the *Schizochytrium* strain is 90-95%.

The starting strain is subjected to mutagenesis and multiple screenings to obtain a strain with high oil yield and high Sn-2 position DHA content.

It should be understood by those skilled in the art that the percentage of the triglyceride with DHA at the Sn-2 position is used as an indicator for the screening of a desired high yield strain.

The content of Sn-2 fatty acids is determined according to the method recited in GB/T 24984-2010/ISO 6800:1997 "Animal and Vegetable Fats and Oils—Determination of the Composition of Fatty Acids in the 2-position of the Triglyceride Molecules".

In order to obtain a strain with high stability, the screened strain can also be evaluated for genetic stability. It has been accepted in the verification of genetic stability in the modern breeding that if the strain obtained from the mutation breeding can still meet the expected requirements of biological characteristics after five passages, it is considered to have high stability.

Through the mutagenesis, screening and genetic stability evaluation mentioned above, a strain with high yield of the Sn-2 DHA is obtained.

The *Schizochytrium* strain of the present disclosure has been deposited in Guangdong Microbial Culture Collection Center (GDMCC, Guangdong Institute of Microbiology, 5th Floor, No. 59 Building, No. 100 Xianliezhong Road, Guangzhou, 510070, China) on Aug. 8, 2019 with an accession number of GDMCC No. 60733.

After the fermentation, the *Schizochytrium* strain provided herein can produce an Sn-2 DHA-rich microbial oil, and the fermentation method has no special requirements as long as it enables the proliferation of the *Schizochytrium* strain.

There are no special requirements for the fermentation by the *Schizochytrium* strain. In some embodiments, the fermentation is performed at pH 6-7.5 and 27-31° C. for 4-8 days under a ventilation rate of 0.5-1.1 vvm.

When the *Schizochytrium* strain is inoculated in the form of a seed liquid, the inoculation amount can be selected in a wide range, such as 5-10% (v/v).

The fermentation medium used herein can be a medium commonly used in the art for the fermentation by the *Schizochytrium* strain. In an embodiment, the fermentation medium includes a carbon source, a nitrogen source, an inorganic salt, a trace element and a vitamin.

The carbon source is glucose, sucrose, or other substances that can provide a carbon source or a combination thereof, and the nitrogen source is sodium glutamate, yeast powder, yeast extract or other substances that can provide a nitrogen source or a combination thereof.

In some embodiments, the carbon source is selected from the group consisting of glucose, sucrose and a combination thereof.

In some embodiments, the nitrogen source is selected from the group consisting of sodium glutamate, yeast powder, yeast extract and a combination thereof.

In some embodiments, the inorganic salt is selected from the group consisting of calcium salt, phosphate, potassium salt, sodium salt, magnesium salt, ammonium salt and a combination thereof.

In some embodiments, the trace element is selected from the group consisting of nickel, copper, molybdenum, cobalt, zinc, iron, manganese and a combination thereof.

In some embodiments, the vitamin is selected from the group consisting of vitamin $B_1$, vitamin $B_{12}$, vitamin $B_6$, calcium pantothenate, biotin and a combination thereof.

The carbon source, nitrogen source and inorganic salt can be directly added to a medium. However, when a volume of the medium is small, it is difficult to directly add the trace element and the vitamin to the medium, and at this time, the trace element and the vitamin are often prepared into a mother liquor to be added.

Contents of each component in the trace-element mother liquor can be selected within a wide range. In some embodiments, the trace-element mother liquor contains 1-3 g/L of nickel sulfate, 1-3 g/L of copper sulfate, 0.02-0.08 g/L of sodium molybdate, 2-4 g/L of manganese chloride, 0.02-0.08 g/L of cobalt chloride, 2-4 g/L of zinc sulfate and 8-10 g/L of ferrous sulfate.

Contents of each component in a vitamin mother liquor can be selected within a wide range. In some embodiments, the vitamin mother liquor contains 9-11 g/L of vitamin $B_1$, 0.1-0.3 g/L of vitamin $B_{12}$, 2-4 g/L of calcium pantothenate and 0.005-0.01 g/L of biotin.

In some embodiments, the nitrogen source in the fermentation medium includes glutamate.

A concentration of the glutamate can be selected in a wide range. In some embodiments, the concentration of the glutamate in the fermentation medium is 5-15 g/L.

A concentration of the carbon source can be selected in a wide range. In some embodiments, the concentration of the carbon source in the fermentation medium is 5-70 g/L.

In an embodiment, the fermentation medium contains 5-70 g/L of the carbon source, 15-45 g/L of the nitrogen source, 5-40 g/L of the inorganic salt, 0.01-0.04 g/L of the trace element and 0.01-0.04 g/L of the vitamin, preferably 40-60 g/L of the carbon source, 20-35 g/L of the nitrogen source, 10-25 g/L of the inorganic salt, 0.015-0.035 g/L of the trace element and 0.01-0.03 g/L of the vitamin.

In an embodiment, the fermentation medium further includes 0.1-0.5 g/L of an anti-foaming agent.

During the fermentation process, the addition of the carbon source and the nitrogen source is continuously performed to adjust the carbon-to-nitrogen ratio. When approaching the fermentation end, the carbon source is not supplied into the medium any more so that the residual sugar is reduced to 0. In this way, an auxotrophic condition is formed by adjusting the carbon-to-nitrogen ratio to improve the oil production of the *Schizochytrium* strains.

In order to increase a yield of the fermentation product, in some embodiments, the method includes: activating the *Schizochytrium* strain by shake flask culture to obtain a seed liquid; and inoculating the seed liquid into a seed culture medium followed by transferring to a fermentation medium for the fermentation. In some embodiments, the method includes: inoculating the *Schizochytrium* strain into an activation medium for activation to obtain an activated *Schizochytrium* suspension; inoculating the activated *Schizochytrium* suspension into a seed culture medium for proliferation to obtain a seed liquid; and inoculating the seed liquid into the fermentation medium for the fermentation to produce the microbial oil.

The *Schizochytrium* strain provided herein is preserved in an ampoule or a glycerin tube.

In some embodiments, in the activating process, the *Schizochytrium* strains stored in a frozen glycerin tube are thawed and inoculated into an activation medium for activation.

The activation can be performed once or multiple times to prepare the activated *Schizochytrium* suspension.

The activation conditions can be selected in a wide range. In some embodiments, the activation is carried out at 27.5-28.5° C. and 150-200 r/min for 48-72 hours.

Preferably, the activation medium includes a carbon source, a nitrogen source, an inorganic salt, a trace element and a vitamin. In an embodiment, the activation medium contains 30-50 g/L of the carbon source, 25-45 g/L of the nitrogen source, 25-40 g/L of the inorganic salt, 0.015-0.025 g/L of the trace element and 0.01-0.02 g/L of the vitamin.

In an embodiment, the activation is performed through steps of: thawing the *Schizochytrium* strain stored in a frozen glycerin tube followed by inoculation into a sterilized activation medium using a sterile pipette; and culturing the *Schizochytrium* strain at 27.5-28.5° C. and 150-200 r/min for 48-72 hours. In an embodiment, the activation medium contains 30-50 g/L of a carbon source, 25-45 g/L of a nitrogen source, 25-40 g/L of an inorganic salt, 0.015-0.025 g/L of a trace element and 0.01-0.02 g/L of a vitamin.

Preferably, the strain in one tube is inoculated into 4-6 500 mL flasks each containing 200-300 mL of the activation medium.

In the expansion culture, the activated *Schizochytrium* suspension is inoculated into a seed culture medium for expansion to obtain a seed liquid.

Preferably, the expansion culture is carried out at 27-28.5° C. under a ventilation rate of 0.5-0.8 vvm for 48-72 hours.

Preferably, the seed culture medium includes 25-60 g/L of a carbon source, 10-30 g/L of a nitrogen source, 15-35 g/L of an inorganic salt, 0.01-0.02 g/L of a trace element and 0.01-0.02 g/L of a vitamin.

Preferably, the seed culture medium further includes 0.1-0.5 g/L of an anti-foaming agent.

In an embodiment, the expansion culture is performed through steps of: inoculating the activated *Schizochytrium* suspension into a primary seed culture medium for primary expansion followed by inoculation into a secondary seed culture medium for secondary propagation to obtain the seed liquid.

Preferably, the primary expansion is carried out at 27-28.5° C. under a ventilation rate of 0.5-0.8 vvm for 48-60 hours.

Preferably, the secondary propagation is carried out at 27-28.5° C. under a ventilation rate of 0.5-0.8 vvm for 12-24 hours.

Preferably, the primary seed culture medium contains 25-35 g/L of the carbon source, 10-30 g/L of the nitrogen source, 15-35 g/L of the inorganic salt, 0.01-0.02 g/L of the trace element and 0.01-0.02 g/L of the vitamin.

Preferably, the secondary seed culture medium contains 40-60 g/L of the carbon source, 10-15 g/L of the nitrogen source, 15-20 g/L of the inorganic salt, 0.01-0.02 g/L of the trace element and 0.01-0.02 g/L of the vitamin.

Types of components of the activation medium and the seed culture medium are the same as those of the fermentation medium, The present disclosure may further process the above-mentioned fermentation product to obtain a microbial oil. There are no special requirements for the processing method as long as the method can extract the microbial oil from the fermentation product. In order to improve the production of the microbial oil, the fermentation product is subjected to wall breaking and extraction.

In a third aspect, the present disclosure provides a microbial oil prepared by the above method, including a triglyceride, where Sn-2 fatty acids of the triglyceride includes 23% or more by weight of DHA.

Preferably, a weight percentage of total DHA in the microbial oil is not less than 38%.

In a fourth aspect, the present disclosure provides a food including the above-mentioned microbial oil.

The food is infant formula food, nutraceutical or health food.

In a fifth aspect, the present disclosure provides a *Schizochytrium* strain with an accession number of GDMCC No. 60733.

The method for obtaining the *Schizochytrium* strain is described in the second aspect, and will not be repeated here.

In a sixth aspect, the present disclosure provides a use of the *Schizochytrium* strain in the production of the above-mentioned microbial oil.

Preferably, the microbial oil includes a triglyceride, where Sn-2 fatty acids of the triglyceride include 23% or more by weight of DHA.

Preferably, a weight percentage of total DHA in the microbial oil is not less than 38%.

The present disclosure will be further described in detail below with reference to the embodiments.

In the embodiments, a content of DHA and a fatty acid composition in a microbial oil are detected according to GB26400-2011 and GB 5009.168-2016, respectively.

The absorption rate of DHA in human body is detected by an efficacy trial, where male and female subjects are required to take in the microbial oil produced by the method of the present disclosure and a control DHA oil, and then blood samples are collected to determine a content of the DHA and a content of the Sn-2 DHA in the blood to calculate the absorption rate of DHA.

The conventional *Schizochytrium* strain is provided by China Center of Industrial Culture Collection, and has an accession number of CICC 11091s.

The glucose, sucrose, yeast powder, sodium glutamate, yeast extract, sodium chloride, magnesium sulfate, calcium chloride, potassium dihydrogen phosphate, nickel sulfate, copper sulfate, sodium molybdate, cobalt chloride, zinc sulfate, ferrous sulfate, manganese chloride, vitamin $B_1$, vitamin $B_{12}$, vitamin $B_6$, calcium pantothenate, biotin, sodium bicarbonate, sodium sulfate, ammonium sulfate and potassium chloride are all commercially available.

In the embodiments, the trace-element mother liquor contains 2 g/L of nickel sulfate, 1.9 g/L of copper sulfate, 0.04 g/L of sodium molybdate, 2.8 g/L of manganese chloride, 0.04 g/L of cobalt chloride, 3.2 g/L of zinc sulfate and 9 g /L of ferrous sulfate; and the vitamin mother liquor contains 10.3 g/L of vitamin $B_1$, 0.16 g/L of vitamin $B_{12}$, 3.2 g/L of calcium pantothenate and 0.008 g/L of biotin.

PREPARATION EXAMPLE

Preparation of *Schizochytrium* Strain (GDMCC No. 60733)

A parent strain preserved in the ampoule was inoculated into an activation medium and activated at 28° C. for 2 days, where the activation medium contained 40 g/L of glucose, 31 g/L of sodium glutamate, 19 g/L of sodium chloride, 5.8 g/L of yeast extract, 8 g/L of magnesium sulfate, 5.7 g/L of potassium dihydrogen phosphate, 1 g/L of trace element and 1 g/L of vitamin (the activation medium plate further contained 18 g/L of agar).

The activated *Schizochytrium* suspension was spread on an activation medium plate, and then subjected to ARTP mutagenesis in a multifunctional mutagenesis system (MPMS) produced by Adhoc Interteck Co., Ltd. (Beijing, China), where the ARTP mutagenesis was carried out at a plasma mutagenesis power of 100 W, a gas flow rate of 10 SLM and a treatment distance of 2 mm for 25 s; the *Schizochytrium* suspension used for the mutagenesis had an $OD_{600}$ of 0.6-0.8 or a concentration of $10^6$-$10^8$ cfu/mL; and a lethality rate was 92.54%. Well-grown single colonies were selected for passage, and then inoculated into a shake flask containing the activation medium and cultured at 27° C. for 4 days. A preliminary screening was performed to detect a content of DHA and a content of the Sn-2 position DHA in the culture to select high-yield strains. The high-yield strains obtained by the preliminary screening were subjected to secondary screening by culture in a shake flask at 27° C. for 4 days to further select high-yield strains. The genetic stability of the high-yield strains obtained by the secondary screening was investigated. After 5 passages, the strain with stable genetic traits was used as the production strain and stored for long-term use.

After screening, the *Schizochytrium* strain GDMCC No. 60733 of the present disclosure was obtained, which had been deposited in Guangdong Microbial Culture Collection Center (GDMCC, Guangdong Institute of Microbiology, 5th Floor, No. 59 Building, No. 100 Xianliezhong Road, Guangzhou, 510070, China) on Aug. 8, 2019.

Example 1

30 L Fermentation and Production Using the *Schizochytrium* Strain GDMCC No. 60733

An activation medium used herein contained 40 g/L of glucose, 31 g/L of sodium glutamate, 5.8 g/L of yeast extract, 19 g/L of sodium chloride, 8 g/L of magnesium sulfate, 5.7 g/L of potassium dihydrogen phosphate, 1 g/L of trace element and 1 g/L of vitamin.

A seed culture medium used herein contained 30 g/L of glucose, 6.3 g/L of sodium glutamate, 8.3 g/L of yeast extract, 8.3 g/L yeast powder, 1.45 g/L of sodium chloride, 5.18 g/L of magnesium sulfate, 1.66 g/L of potassium dihydrogen phosphate, 0.25 g/L of calcium chloride, 0.25 g/L of sodium bicarbonate, 9.34 g/L of sodium sulfate, 1.04 g/L of ammonium sulfate, 0.83 g/L of potassium chloride, 1 g/L of trace element, 1 g/L of vitamin and 0.3 g/L of a defoamer.

A fermentation medium used herein contained 50 g/L of glucose, 15 g/L of sodium glutamate, 10.9 g/L of yeast extract, 2.6 g/L of sodium chloride, 5.8 g/L of magnesium sulfate, 2.4 g/L of potassium dihydrogen phosphate, 0.25 g/L of calcium chloride, 0.22 g/L of sodium bicarbonate, 3.62 g/L of sodium sulfate, 1.13 g/L of ammonium sulfate, 0.94 g/L of potassium chloride, 1.1 g/L of a trace-element mother liquor, 1.1 g/L of a vitamin mother liquor and 0.19 g/L of a defoamer.

The fermentation was performed as follows.

(1) An ordinary *Schizochytrium* strain and the *Schizochytrium* strain GDMCC No. 60733 were activated, respectively. Specifically, the *Schizochytrium* strain stored in each frozen glycerin tube was thawed and inoculated into four shake flasks containing 200 mL of the activation medium, and cultured on a shaker at 28° C. and 180 r/min for 48 hours to obtain an activated *Schizochytrium* suspension.

(2) The activated *Schizochytrium* suspension obtained from step (1) was inoculated into a shake flask containing 200 mL of the activation medium at 3% (v/v), and cultured on a shaker at 28° C. and 180 r/min for 72 hours for proliferation.

(3) 200 mL of the culture obtained from step (2) was inoculated into a seed tank containing 3 L of the seed culture medium, and cultured at 28° C., 0.03 MPa and 180 r/min under a ventilation rate of 0.6 vvm for 50 hours.

(4) All of the culture in the seed tank was inoculated into a fermentation tank containing 14 L of the fermentation medium, and cultured at pH 6.8 and 29° C. at a rotation speed of 140 r/min for 5-6 days, where the ventilation rate and the tank pressure were controlled at 0.95 vvm and 0.03 MPa, respectively. During the fermentation, a sterile glucose solution (250 g/L) and a sterile sodium glutamate solution (250 g/L) were added in fed-batch to maintain the glutamate concentration at 5-8 g/L and the carbon source concentration at 10-23 g/L. After 96 hours of the fermentation, the supply of carbon source and glutamate was stopped to obtain a fermentation broth.

(5) 5 L of the fermentation broth obtained from step (4) was subjected to enzymatic wall disruption, and then centrifuged by a high speed centrifuge to separate a water phase, a solid phase, and an oil phase to obtain a microbial oil.

(6) The microbial oil obtained from step (5) was analyzed to obtain a content of DHA, fatty acid composition and a weight percentage of DHA at the Sn-2 position of the triglyceride, and the results were showed in Table 1.

TABLE 1

Parameters of the microbial oils in Example 1

|  | Ordinary Schizochytrium strain | Schizochytrium strain GDMCC No. 60733 |
|---|---|---|
| DHA (C22:6), g/100 g | 40.256 | 43.139 |
| Palmitic acid (C16:0), g/100 g | 21.894 | 20.974 |
| Stearic acid (C18:0), g/100 g | 1.542 | 1.301 |
| Oleic acid (C18:1), g/100 g | 0.312 | 0.273 |
| Docosapentaenoic acid (C22:5), g/100 g | 11.012 | 10.330 |
| Weight percentage of DHA at Sn-2 position of triglyceride, % | 21.97 | 43.24 |
| Weight percentage of DHA at Sn-1 and Sn-3 positions of triglyceride, % | 56.98 | 47.55 |
| Absorption rate of DHA, % | 44.17 | 61.8 |

Example 2

100 L Fermentation and Production Using *Schizochytrium* Strain GDMCC No. 60733

An activation medium used herein contained 30 g/L of glucose, 20 g/L of sodium glutamate, 5 g/L of yeast extract, 15 g/L of sodium chloride, 6 g/L of magnesium sulfate, 4 g/L of potassium dihydrogen phosphate, 0.8 g/L of trace element and 0.75 g/L of vitamin.

A seed culture medium used herein contained 25 g/L of glucose, 5.5 g/L of sodium glutamate, 7 g/L of yeast extract, 7 g/L of yeast powder, 1.1 g/L of sodium chloride, 4 g/L of magnesium sulfate, 1.2 g/L of potassium dihydrogen phosphate, 0.15 g/L of calcium chloride, 0.15 g/L of sodium bicarbonate, 7 g/L of sodium sulfate, 0.8 g/L of ammonium sulfate, 0.6 g/L of potassium chloride, 0.8 g/L of trace element, 0.75 g/L of vitamin and 0.2 g/L of a defoamer.

A fermentation medium used herein contained 30 g/L of glucose, 10 g/L of sucrose, 12 g/L of sodium glutamate, 9 g/L of yeast extract, 2 g/L of sodium chloride, 4.5 g/L of magnesium sulfate, 2 g/L of potassium dihydrogen phosphate, 0.2 g/L of calcium chloride, 0.2 g/L of sodium bicarbonate, 2.8 g/L of sodium sulfate, 1 g/L of ammonium sulfate, 0.8 g/L of potassium chloride, 0.9 g/L of trace element, 0.9 g/L of vitamin and 0.15 g/L of a defoamer.

The specific steps were shown as follows.

(1) The ordinary *Schizochytrium* strain and the *Schizochytrium* strain GDMCC No. 60733 were activated, respectively. The *Schizochytrium* strain stored in each frozen glycerin tube was thawed and inoculated into five shake flasks each containing 200 mL of the activation medium, and cultured on a shaker at 28.5° C. and 150 r/min for 72 hours to obtain an activated *Schizochytrium* suspension.

(2) Two shake flasks of the activated *Schizochytrium* suspension obtained from step (1) were inoculated into five shake flasks each containing 200 mL of the activation medium, and cultured on a shaker at 28° C. and 150 r/min for 48 hours.

(3) 400 mL of the culture obtained from step (2) was inoculated into a seed tank containing 6 L of the seed culture medium, and cultured at 28° C. and 150 r/min for 48 hours, where a ventilation rate and a tank pressure were controlled at 0.5 vvm and 0.03 MPa, respectively.

(4) All of the culture in the seed tank was inoculated into a fermentation tank containing 45 L of the fermentation medium, and cultured at 28-29° C. and 90-120 r/min for 5-6 days, where a ventilation rate and a tank pressure were controlled at 0.5-0.8 vvm and 0.03 MPa, respectively. During the fermentation, a sterile glucose solution (250 g/L) and a sterile sodium glutamate solution (250 g/L) were added in fed-batch to maintain a concentration of glutamate at 8-12 g/L and a concentration of carbon source at 40-65 g/L. After 96 hours of the fermentation, the supply of carbon source and glutamate was stopped to obtain a fermentation broth.

(5) 10 L of the fermentation broth obtained from step (4) was subjected to enzymatic wall disruption, and then centrifuged by a high speed centrifuge to obtain a microbial oil.

(6) The microbial oil obtained from step (5) was analyzed to obtain a content of DHA, a fatty acid composition and a weight percentage of DHA at the Sn-2 position of triglyceride, and the results were showed in Table 2.

TABLE 2

Parameters of the microbial oils in Example 2

|  | Ordinary Schizochytrium strain | Schizochytrium strain GDMCC No. 60733 |
|---|---|---|
| DHA(C22:6), g/100 g | 42.689 | 46.786 |
| Palmitic acid (C16:0), g/100 g | 23.13 | 21.05 |
| Stearic acid (C18:0), g/100 g | 1.56 | 1.31 |
| Oleic acid (C18:1), g/100 g | 0.314 | 0.271 |
| Docosapentaenoic acid (C22:5), g/100 g | 11.012 | 10.301 |
| Weight percentage of DHA at Sn-2 position of triglyceride, % | 22.76 | 43.68 |
| Weight percentage of DHA at Sn-1 and Sn-3 positions of triglyceride, % | 57.37 | 46.68 |
| Absorption rate of DHA, % | 43.98 | 62.8 |

Example 3

45 m³ Industrial Fermentation and Production Using *Schizochytrium* Strain GDMCC No. 60733

A seed culture medium used herein contained 50 g/L of glucose, 35 g/L of sodium glutamate, 10 g/L of yeast extract, 22 g/L of sodium chloride, 10 g/L of magnesium sulfate, 8 g/L of potassium dihydrogen phosphate, 1.4 g/L of trace element and 1.5 g/L of vitamin.

A primary seed culture medium used herein contained 35 g/L of glucose, 8 g/L of sodium glutamate, 10 g/L of yeast extract, 10 g/L of yeast powder, 1.9 g/L of sodium chloride, 6 g/L of magnesium sulfate, 2.1 g/L of potassium dihydrogen phosphate, 0.4 g/L of calcium chloride, 0.4 g/L of sodium bicarbonate, 12 g/L of sodium sulfate, 1.3 g/L of ammonium sulfate, 1.1 g/L of potassium chloride, 1.2 g/L of trace element, 1.2 g/L vitamin and 0.4 g/L of a defoamer.

A secondary seed culture medium was: 50 g/L of glucose, 5.65 g/L of sodium glutamate, 5.65 g/L of yeast extract, 1.3 g/L of sodium chloride, 4.65 g/L of magnesium sulfate, 1.49 g/L of potassium dihydrogen phosphate, 0.22 g/L of calcium chloride, 0.22 g/L of sodium bicarbonate, 8.39 g/L of sodium sulfate, 0.93 g/L of ammonium sulfate, 0.74 g/L of potassium chloride, 0.93 g/L of trace element, 0.93 g/L of vitamin and 0.3 g/L of a defoamer.

A fermentation medium used herein contained 40 g/L of glucose, 20 g/L of sucrose, 20 g/L of sodium glutamate, 12 g/L of yeast extract, 3.2 g/L of sodium chloride, 7 g/L of magnesium sulfate, 3 g/L of potassium dihydrogen phosphate, 0.4 g/L of calcium chloride, 0.3 g/L of sodium bicarbonate, 4.5 g/L of sodium sulfate, 1.5 g/L of ammonium sulfate, 1.2 g/L of potassium chloride, 1.6 g/L of trace element and 1.6 g/L of vitamin.

The specific steps of the fermentation were shown as follows.

(1) The ordinary *Schizochytrium* strain and the *Schizochytrium* strain GDMCC No. 60733 were activated, respectively. The *Schizochytrium* strain stored in each frozen glycerin tube were thawed and inoculated into six shake flasks containing 200 mL of the activation medium, and cultured on a shaker at 28° C. and 180 r/min for 60 hours to obtain an activated *Schizochytrium* suspension.

(2) Two shake flasks of the activated *Schizochytrium* suspension obtained from step (1) were inoculated into five flasks each containing 200 mL of the activation medium, and cultured on a shaker at 28±0.5° C. and 180 r/min for 60 hours for proliferation.

(3) 500 L of the primary seed culture medium was sterilized and cooled to 40° C. or lower, and then transferred to a primary seed tank. 1 L of the culture obtained from step (2) was inoculated into the primary seed tank, and cultured at pH 6.8, 28±0.5° C. and 150 r/min for 55 hours.

(4) 6 m³ of the secondary seed culture medium was sterilized and cooled to 40° C. or lower, and then transferred to a secondary seed tank. All of the culture in the primary seed tank was aseptically inoculated into the secondary seed tank, and cultured at pH 6.8, 28±0.5° C. and 150 r/min for 18 hours.

(5) 22 m³ of the fermentation medium was sterilized and cooled to 40° C. or lower, and then transferred to a fermentation tank. All of the culture in the secondary seed tank was inoculated into the fermentation tank, and cultured at pH 7.5, 28±0.5° C. and 100 r/min for 5 days, where a ventilation rate was controlled at 1.0 vvm. During the fermentation, a sterile glucose solution (250 g/L) and a sterile sodium glutamate solution (250 g/L) were added in fed-batch to maintain a concentration of glutamate at 12-15 g/L and a concentration of carbon source at 55-70 g/L. After 96 hours of the fermentation, the supply of carbon source and glutamate was stopped to obtain a fermentation broth.

(6) The fermentation broth was subjected to enzymatic wall disruption, preheated to 85-90° C., and then centrifuged by a triple-phase centrifuge to obtain a microbial oil.

(7) The microbial oil obtained from step (6) was analyzed to obtain a content of DHA, a fatty acid composition of and a weight percentage of DHA at the Sn-2 position of triglyceride, and the results were showed in Table 3.

TABLE 3

Parameters of the microbial oils in Example 3

| | Ordinary *Schizochytrium* strain | *Schizochytrium* strain GDMCC No. 60733 |
|---|---|---|
| DHA (C22:6), g/100 g | 45.768 | 50.664 |
| Palmitic acid (C16:0), g/100 g | 22.913 | 20.859 |
| Stearic acid (C18:0), g/100 g | 1.321 | 1.293 |
| Oleic acid (C18:1), g/100 g | 0.314 | 0.277 |
| Docosapentaenoic acid (C22:5), g/100 g | 12.435 | 10.366 |
| Weight percentage of DHA at Sn-2 position of triglyceride, % | 22.148 | 43.96 |
| Weight percentage of DHA at Sn-1 and Sn-3 positions of triglyceride, % | 54.56 | 46.33 |
| Absorption rate of DHA, % | 44.78 | 63.1 |

The above-mentioned embodiments are only preferred embodiments, and not intend to limit the scope of the present disclosure. It should be noted that variations and modifications made by those skilled in the art without departing from the spirit of the disclosure should fall within the scope of the present disclosure.

What is claimed is:

1. A method for producing a microbial oil, comprising:
performing an atmospheric room temperature plasma (ARTP) mutagenesis on a starting strain in a form of a bacterial suspension for 5-60 seconds at a plasma mutagenesis power of 80-120 W, a gas flow rate of 8-12 standard liter per minute (SLM) and a treatment distance of 1-3 mm, followed by a screening to obtain a *Schizochytrium* strain; and
inoculating the *Schizochytrium* strain into a fermentation medium for fermentation to produce the microbial oil;
wherein the *Schizochytrium* strain is *Schizochytrium* sp. GDMCC No. 60733;
the fermentation is carried out at pH 6-7.5 and 27-31° C. for 4-8 days under a ventilation rate of 0.45-1.1 vvm;
the fermentation medium comprises 5-70 g/L of a carbon source, 15-45 g/L of a nitrogen source, 5-40 g/L of an inorganic salt, 0.01-0.04 g/L of a trace element and 0.01-0.04 g/L of a vitamin; and
the nitrogen source comprises glutamate; and a concentration of glutamate in the fermentation medium is 5-15 g/L; and
the method further comprising:
inoculating the *Schizochytrium* sp. GDMCC No. 60733 into an activation medium for activation to obtain an activated Schizochytrium suspension;
inoculating the activated Schizochytrium suspension into a seed culture medium for expansion culture to obtain a seed liquid; and
inoculating the seed liquid into the fermentation medium for the fermentation to produce the microbial oil;
wherein the activation is carried out at 27.5-28.5° C. and 150-200 r/min for 48-72 hours;
the activation medium comprises 30-50 g/L of a carbon source, 25-45 g/L of a nitrogen source, 25-40 g/L of an inorganic salt, 0.015-0.025 g/L of a trace element and 0.01-0.02 g/L of a vitamin;
the expansion culture is carried out at 27-28.5° C. under a ventilation rate of 0.5-0.8 vvm for 48-72 hours; and
the seed culture medium comprises 25-60 g/L of a carbon source, 10-30 g/L of a nitrogen source, 15-35 g/L of an inorganic salt, 0.01-0.02 g/L of a trace element and 0.01-0.02 g/L of a vitamin.

2. The method of claim 1, wherein the carbon source in the fermentation medium, the carbon source in the activation medium and the carbon source in the seed culture medium are independently selected from the group consisting of glucose, sucrose and a combination thereof;
- the nitrogen source in the fermentation medium, the nitrogen source in the activation medium and the nitrogen source in the seed culture medium are independently selected from the group consisting of sodium glutamate, yeast powder, yeast extract and a combination thereof;
- the inorganic salt in the fermentation medium, the inorganic salt in the activation medium and the inorganic salt in the seed culture medium are independently selected from the group consisting of calcium salt, phosphate, potassium salt, sodium salt, magnesium salt, ammonium salt and a combination thereof;
- the trace element in the fermentation medium, the trace element in the activation medium and the trace element in the seed culture medium are independently selected from the group consisting of nickel, copper, molybdenum, cobalt, zinc, iron, manganese and a combination thereof; and/or
- the vitamin in the fermentation medium, the vitamin in the activation medium and the vitamin in the seed culture medium are independently selected from the group consisting of vitamin $B_1$, vitamin $B_{12}$, vitamin $B_6$, calcium pantothenate, biotin and a combination thereof.

3. The method of claim 1, further comprising:
- subjecting a product of the fermentation to extraction to produce the microbial oil.

\* \* \* \* \*